(12) United States Patent
Williams

(10) Patent No.: US 9,107,402 B2
(45) Date of Patent: Aug. 18, 2015

(54) COMPOSITION AND METHOD TO MODIFY SPERM FERTILITY AND FEMALE GENDER RATIO IN MAMMALS

(76) Inventor: Timothy James Williams, Arcola, IL (US)

( * ) Notice: Subject to any disclaimer, the term of this patent is extended or adjusted under 35 U.S.C. 154(b) by 1057 days.

(21) Appl. No.: 12/286,887

(22) Filed: Oct. 3, 2008

(65) Prior Publication Data

US 2010/0087702 A1 Apr. 8, 2010

(51) Int. Cl.
*A01N 1/02* (2006.01)

(52) U.S. Cl.
CPC ................................ *A01N 1/0226* (2013.01)

(58) Field of Classification Search
CPC .................................................. A01N 1/0226
USPC ........................................... 600/35; 424/94.1
See application file for complete search history.

(56) References Cited

PUBLICATIONS

Kimura et al., Effects of D-glucose concentration, D-fructose, and inhibitors of enzymes of the pentose phosphate pathway on the development and sex ratio of bovine blastocysts, Molecular Reproduction and Development, vol. 72, p. 201-207, 2005.*

Urner et al., A possible role for the pentose phosphate pathway of spermatozoa in gamete fusion in the mouse., Biology of Reproduction, vol. 60, p. 733-739, 1999.*

Sarkar et al., Glucose-6-phosphate dehydrogenase (G6PD) activity of human sperm, Journal of Medical Genetics, vol. 14, p. 250-255, 1977.*

Urner et al., Involvement of the pentose phosphate pathway and redox regulation in fertilization in the mouse, Molecular Reproduction and Development, vol. 70, p. 494-503, 2005.*

Tiffin et al., Glucose and glutamine metabolism in pre-attachment cattle embryos in relation to sex and stage of development, Journal of Reproduction and Fertility, vol. 93, p. 125-132, 1991.*

* cited by examiner

*Primary Examiner* — Taeyoon Kim
*Assistant Examiner* — Tiffany Gough

(57) ABSTRACT

A composition and method is provided to modify sperm fertility and sex ratio of mammalian offspring. The composition includes an amount of a class of compounds of phenoxazine or phenothiazine, having the structure (see FIG. 1) and ionic derivatives thereof, wherein R1 is H, a lower alkyl group or N (R3)2, R2 is N, S, O, and R3 is H or a lower alkyl group. A second component of the composition is an amount of an electron transfer agent capable of oxidizing a reduced cofactor (NADPH or NADH). A third component of the composition is an amount of a hexose sugar and/or the phosphorylated esters of such. When mixed with living sperm prior to or at the time of insemination, the composition results in modified rates of conception and an alteration of birth sex ratio.

5 Claims, 3 Drawing Sheets

COMPOSITION AND METHOD TO MODIFY SPERM FERTILITY AND FEMALE GENDER RATIO IN MAMMALS

CROSS-REFERENCE TO RELATED APPLICATIONS

Priority is hereby claimed to provisional application 60/995,767 filed Sep. 29, 2007 which is incorporated herein.

STATEMENT REGARDING FEDERALLY SPONSORED RESEARCH OR DEVELOPMENT

"Not Applicable"

REFERENCE TO SEQUENCE LISTING, A TABLE, OR A COMPUTER PROGRAM LISTING COMPACT DISC APPENDIX

"Not Applicable".

BACKGROUND OF THE INVENTION

The present invention relates to compositions and methods for treating sperm for the purpose of modifying sperm function and the gender ratio in offspring of mammalian species. The invention is further directed to a method of using the composition to modify the functionality of mammalian sperm in general and more specifically, to increase sperm fertility for the purpose of enhancing conception. In addition, the invention can be used to modify the fertility of X-chromosome and Y-chromosome bearing sperm and using said sperm in the reproduction processes of artificial insemination (AI), in vitro fertilization (IVF), and embryo transfer (ET) for the purpose of modifying gender in mammals.

It is well documented in mammalian species that the X-chromosome contains a unique set of genes which are highly conserved across mammals as well as other vertebrates. One of the X-linked genes codes for the ubiquitous enzyme, glucose-6-phosphate dehydrogenase (G6PDH). G6PDH is a pivotal enzyme in glucose metabolism and is the primary regulator of the hexose-mono phosphate shunt (HMS), also known as the pentose phosphate shunt (PPP). The main function of the HMS is to produce NADPH, which is necessary for reduction-oxidation reactions and to form ribose-5-phosphate for nucleic acid synthesis.

G6PDH also play an important role in glucose oxidation via glycolysis, a primary source of cellular energy. Glucose metabolism is implicated in the fertilization process in many mammalian species. It is well accepted that glucose metabolism through glycolysis provides energy to sperm. However, the role of glucose metabolism through the hexose-monophosphate shunt (HMS) in spermatozoa is not understood. The existence of an HMS pathway in mouse and human sperm has been documented, but not in other species including ram or bull sperm. However, techniques used for these early studies have come into question and the evidence does not disprove the existence of the HMS in sheep or cattle sperm.

The implications of a functioning HMS in sperm, as found in human and mouse sperm, suggests that sperm need to produce NADPH via the HMS to achieve fertilization. Since NADPH metabolism has been implicated in sperm motility and fertilization, it also suggests that the HMS is a key metabolic pathway in sperm capacitation, the acrosome reaction, and oocyte fusion.

While investigating the role of G6PDH and the HMS as a method to sex mouse embryos, I first used the phenoxazine compound, brilliant cresol blue (BCB) in living embryos to detect and semi-quantify G6PDH activity and successfully transplant these embryo to produce normal living offspring. This study demonstrated that BCB and its metabolites were relatively non-toxic in the early-staged mouse embryos. My studies with bovine embryos revealed similar results.

Prior art teaches that the HMS in bovine oocytes, the phenoxazine/phenothiazine class of compounds can be used to increase glucose oxidation specifically through the Hexose Monophosphate Shunt (HMS) and that BCB stimulates a 15-fold increase in oxidation of glucose through the HMS as well as an increased level of glucose metabolism through the HMS in female embryos.

I also first used the electron transfer agent, NADPH oxioreductase (Diaphorase) to further amplify the HMS in living mouse and cattle embryos No patents concerning the use of phenoxazine/phenothiazine and/or electron transfer agents in living gametes or embryos have arisen from these studies.

It is well documented that early staged female embryos exhibit preferential metabolism of glucose via the HMS. This is due to the presence of two X-chromosomes and elevated levels of G6PDH. However, there is no prior art concerning differential glucose metabolism of X-chromosome and Y-chromosome bearing sperm. Concerning this invention, it is postulated that mammalian sperm (like embryos) retain a HMS pathway and metabolize glucose and more specifically, G-6-P, through this pathway to produce NADPH. It is also postulated that the X-chromosome bearing (female) sperm can preferentially oxidize G-6-P through the HMS pathway due to higher levels of X-linked enzyme, G6PDH, relative to the Y-chromosome bearing (male) sperm. The reason for the sex differential in oxidation of G-6-P is speculative but could have arisen as a mechanism to regulate sex allocation in natural populations. Given this assumption, the X-chromosome bearing (female) sperm is thought to readily oxidize glucose-6-phosphate through the HMS pathway. When sperm are exposed to a chromo-phenoxazine compound, the HMS pathway is promoted and amplified to produce large amounts of NADPH. This amplification occurs until the phenoxazine compound is completely reduced to the leuco-phenoxazine form or the reaction is inhibited due to substrate depletion. With the addition of excess pentose substrate (preferentially G-6-P), the reaction continues until complete phenoxazine reduction. The other major component and potentially rate-limiting to the reaction is NADP+. This cofactor is needed in the first and third steps of the HMS pathway. Endogenous electron transfer agents such as NADPH dehydrogenase or NADPH oxidase are unlikely to be available in sustainable titers. However, with the addition of an exogenous electron transfer agent such as NADPH oxioreductase (usually coupled with a cofactor flavin mononucleotide), the NADPH is oxidized to NADP+ during the transfer of electrons, i.e., the reduction of the chromo-phenoxazine. The NADP+ is then available for reuse in the HMS pathway. Under these conditions, the oxidation of the available pentose sugar, G-6-P, can continue until the substrate becomes limiting or the phenoxazine become completely reduced. The result of the amplification of the HMS are large amounts of reducing power in the form of NADPH which are correlated with increased sperm function, motility, and fertilization capacity. Other substrate precursors such as ribose-5-phosphate, lactate, pyruvate, and NADH would also be generated in high titers and would be available for increased rates of glycolysis, ATP production, and respiration. These precursors could result in increased sperm function, higher motility, and more specifically, increased fertilization capacity for the X-chromosome bearing (female) sperm.

Another observation I have made is that when sperm are exposed to Brilliant Cresol Blue, there is reduced sperm motility and fertility. This loss of motility is postulated to be due to a quenching of the HMS, a shut-down of oxidative phosphorylation, a loss of respiration potential and reduced ATP production. The result is a potential loss of fertilization capacity and sperm viability. In the composition of this invention, it is postulated that the Y-chromosome bearing (male) sperm are exposed to phenoxazine compounds without the benefit of G6PDH. As a result, the male sperm cannot oxidize the available G6P through the HMS pathway and are unable to generate large quantities of NADPH necessary to reduce the chromo-phenoxazine. This in turn results in reduced motility and fertility of the Y-chromosome bearing (male) sperm.

In addition, NADPH oxioreductase may have the opposite effect on the Y-chromosome bearing sperm than what occurs in the X-chromosome bearing sperm. One possibility is that NADPH oxioreductase inhibits glycolysis. This inhibition may be competitive, related to redox potential, or may be due to the high level of specificity of the NADPH oxioreductase enzyme for the NADH that is generated in glycolysis. While the exact mechanism is unknown, it has been observed that the Y-chromosome bearing (male) sperm, when exposed to the composition of this invention, have reduced fertility.

Patent documents of interest concerning methods to preferentially modify sperm function include: U.S. Pat. Nos. 4,191,749, 4,191,749, 4,999,283, 4,788,984, 6,627,655, and 20070166694.

Patent documents of interest concerning the use of phenoxazine BCB in living tissue are limited to in vitro assays, dye indicators, and staining methodology. These include: U.S. Pat. Nos. 6,790,411, 6,867,015, 6,967,015, 6,420,128, and 4,622,395.

Patent documents of interest related to methods of modifying sex ratio in mammals by cell sorting technology include: U.S. Pat. Nos. 6,524,860, 6,372,422, 6,149,867, 6,071,689, and 5,135,759.

Patent documents of interest related to modifying sex ratio in mammals by antigen or antibody sorting include: U.S. Pat. Nos. 6,489,092, 6,153,373, 5,660,997, and 5,439,362.

Terminology

G6PDH: glucose-6-phosphate dehydrogenase
NADP+: tri-phosphopyridine nucleotide
NADPH: beta-nicotinamide adenine dinucleotide phosphate or tri-phosphopyridine nucleotide
NADH: beta-nicotinamide adenine dinucleotide
G-6-P: D-glucose-6-phosphate
6-PG: 6-phosphoglutamate
chromo-Phenoxazine: Phenoxazine (oxidized form)
leuco-Phenoxazine: Phenoxazine (reduced form)
HMS: Hexose monophosphate shunt

BRIEF SUMMARY OF THE INVENTION

In summary, the present invention comprises a composition and method for modifying sperm function, more specifically for modifying sperm motility, capacitation, and/or fertility of the X-chromosome bearing sperm (female) and Y-chromosome bearing sperm (male), and providing a method for modifying sex ratio in mammals by exposing living mammalian sperm prior to artificial insemination to the composition. This composition consists of a chromo-phenoxazine compound wherein said compound is Brilliant Cresyl Blue, 2-methyl-3-diethylamino-7-amino phenoxazine; a phosphorylated hexose ester compound wherein said compound is D-glucose-6-phosphate; and an electron transfer agent wherein said compound is a high molecular weight, proteinaceous oxioreductase enzyme capable of oxidizing the reduced cofactors, NADPH or NADH, and wherein said enzyme is NADPH oxioreductase, ferrodoxin-NADP reductase or lipoic dehydrogenase or Diaphorase.

Cattle, horse, pig, buffalo, alpacas, llamas, dog, cats, goats, and sheep semen are primary examples of such mammalian sperm.

The method comprises a first step of placing a sample of semen, either fresh or frozen, into a vial, ampoule, or tube, or the like together with the composition of matter. The sperm and said composition are mixed and incubated at the appropriate temperature to maintain sperm viability and for a selected time. The temperature is generally at or near body temperature, e.g. 35-39 degrees Celsius for cattle, and the time is generally less than 60 minutes but is experimentally determined, and varies with the species, sperm concentration, volume of the sperm sample, and with other factors such as type of diluent, and whether the sperm have been frozen, chilled, or freshly collected. Successful treatment of the sperm sample is determined by experimental observation. The treated sperm are inseminated by standard artificial methods usually consisting of introducing the sperm sample into the reproductive tract of a receptive female. A second possibility is to introduce the treated sperm into an in vitro fertilization system for the purpose of producing in vitro fertilized embryos for subsequent transfer to a receptive female. A third embodiment is to expose the sperm to the composition immediately preceding the cryopreservation process.

Further, a kit embodiment of the composition of matter and method of application is described.

DETAILED DESCRIPTION OF THE INVENTION

The details of the subject composition, the preparation of composition, and the method of use of the composition are described herein. The subject invention is also described as a kit embodiment and includes the method of use of this embodiment. Before the subject invention is described, it is best understood that the invention is not limited to particular the embodiments described below. Variations of the particular embodiments maybe made and still fall within the scope of the appended claims. It is also to be understood that the terminology employed is for the purpose of describing particular embodiments, and is not intended to be limiting. Instead, the scope of the present invention is established by the appended claims.

Composition

Figure 1:
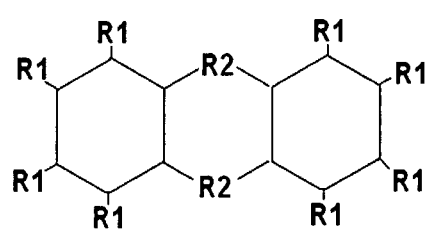
FIG. 1 is a schematic formula of the chromo-phenoxazine and phenothiazine class of compounds, the embodiment having been selected from this class of compounds and having the structure indicated and ionic derivatives thereof, wherein R1 is H, a lower alkyl group or N (R3)2, R2 is N, S, O, and R3 is H or a lower alkyl group.
Figure 2:
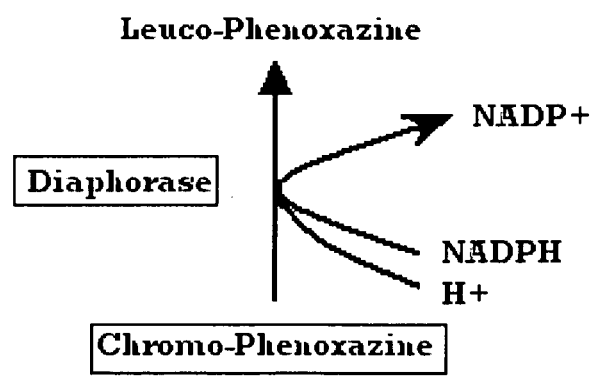
FIG. 2 is diagram of the catalytic engine generated from the chemical reduction of chromo-phenoxazine to leuco-phenoxazine in the presence of the NAD(P)H oxioreductase enzyme (Diaphorase).

The present invention includes within the material components a composition for use within living cells or sperm of mammals. Included within the composition of said embodiment is a phenoxazine or phenothiazine compound having the structure found in FIG. 1 and ionic derivatives thereof, wherein R1 is H, a lower alkyl group or N(R1)2; R2 is N, S, or O; and R3 is H or a lower alkyl group. The primary use of this embodiment within the invention is as an electron accepting agent within living mammalian sperm for the purpose of catalyzing the HMS pathway. FIG. 2 is a diagram of how phenoxazine acts as the catalyst during the metabolism of NADPH to NADP+. The phenoxazine or phenothiazine compounds must be provided in a composition and concentration such that they are non-toxic to living sperm and in the initial composition and the metabolic derivatives such that they exert the required physiological effect. Variants of this use aspect of the invention could be selected from these groups but are not limited to these embodiments; phenoxazine components such as Brilliant Cresyl Blue, i.e., 2-methyl-3 diethylamino-7-amino phenoxazine and related embodiments, e.g., 7-(Diethyl amino)-3-amino-8-methyl-3H-phenoxazine hydrochloride, and 7-Amino-3-(diethyl amino)-2-methylphenoxazine-5-ium chloride, phenoxazine, Capri Blue (C.I. 51000), benzo-a-phenozoxanium (Meldora(medola) Blue), Nile Blue (C.I. 51180), Acid Blue 90, Brilliant Blue G, Brilliant Blue C, Basic Blue 3, and Coomassie Brilliant Blue C-250. Phenothiazine embodiments are Methylene Blue (C.I. 52015), Methylene Green, Azure A, Azure B (C. I. 52010), Azure C, Lauth's Violet (C. I. 52000), Thiocarmine R (C.I. 52035), and Toluidine Blue O.

Figure 3:
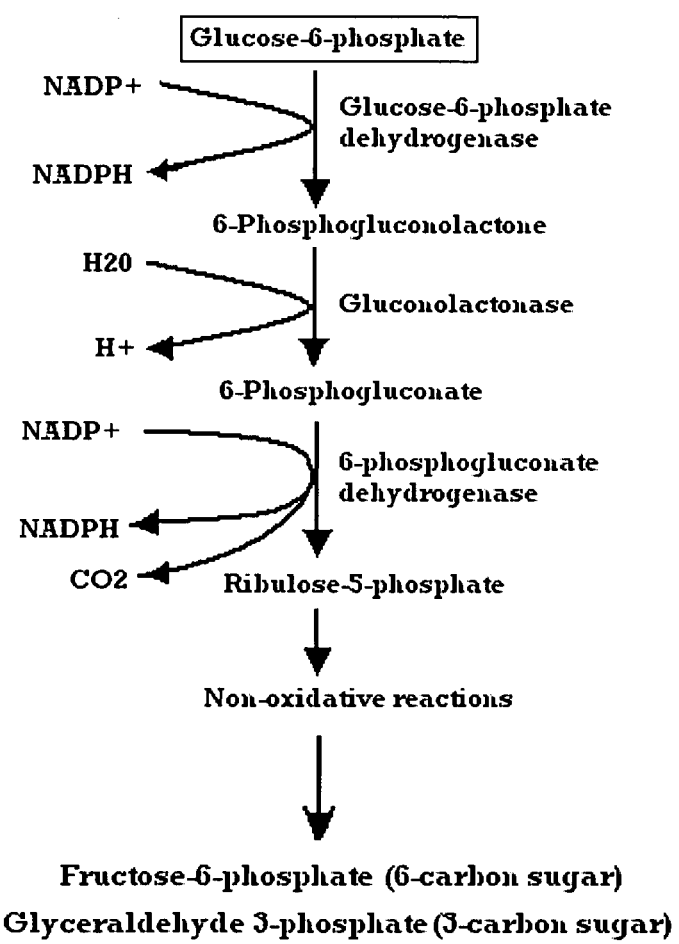
FIG. 3 is a diagram of the HMS pathway through which D-glucose-6-phosphate is oxidized showing the two points of NADPH production from which the chemical reduction of chromo-phenoxazine can catalyze HMS amplification.

The second component of the composition is a hexose sugar or the phosphorylated hexose esters of such which provide an energy source for glycolysis and the HMS pathways. Included hexose reagents are glucose, mannose, fructose, and galactose, and their phosphorylated esters, D-glucose-6-phosphate, fructose-6-phosphate, mannose-6-phosphate, and galactose-6-phosphate. Of primary utility in this invention is D-glucose-6-phosphate (G-6-P). As shown in FIG. 3, G-6-P becomes the primary hydrogen donor for the production of beta-nicotinamide adenine dinucleotide phosphate (NADPH) in the HMS pathway. The oxidation of D-glucose-6-phosphate is regulated by the X-chromosome linked enzyme, glucose-6-phosphate dehydrogenase (G6PDH). As such, the specific activity of G6PDH is the primary regulator of the HMS.

The compound, D-glucose-6-phosphate, likely plays a dual role in this embodiment, acting as the oxidative substrate for the HMS pathway; and also as the inducer of the hexose monophosphate transport system in sperm cells. Incubation of cells in a hexose-6-phosphate compound at the appropriate media concentrations can cause induction of a hexose monophosphate transport system and cellular uptake of D-glucose-6-phosphate. This uptake is independent of the glucose transport system requiring phosphorylation of glucose. Examples of known hexose monophosphate transport inducers are mannose-6-phosphate, fructose-6-phosphate, and D-glucose-6-phosphate. As stated above, this component should be provided in purity and concentration such that it is non-toxic to living mammalian cells and sperm, but yet has the needed physiological consequence.

A third component of the composition is an electron transport agent. The electron transfer agent is a compound or molecule that transfers an electron, such as the hydride ion, from a reduced enzyme cofactor, beta-nicotinamide adenine dinucleotide phosphate (NADPH) or beta-nicotinamide adenine dinucleotide (NADH) to the electron accepting agent in this composition, i.e., the chromo-phenoxazine compound. The electron transport agents of interest are the high molecular weight electron transfer agents. In this specification, high molecular weight means a molecular weight in excess of 2000 daltons and in many embodiments would exceed 5000-20000 daltons. The high molecular weight electron transfer agents are proteinaceous enzymes specifically capable of oxidizing the reduced cofactor, NADH and/or NADPH. Examples are the electron transfer enzyme, NAD(P)H oxidoreductase, found in numerous moieties such as diaphorase, lipoic dehydrogenase, ferrodoxin-NADP reductase, lipoamide dehydrogenase, and NADPH dehydrogenase. Note: Commercially available preparations of the proteinaceous enzyme agents routinely contain small amounts of associated low-molecular weight electron transfer agents, e.g. riboflavin and flavin mononucleotide.

FIG. 2 illustrates the role of the electron transfer agent, diaphorase, in the catalytic reduction of chromo-phenoxazine. The transfer of electrons from NADPH to the chromo-phenoxazine is promoted by the enzyme, diaphorase, producing NADP+. This NADP+ is then recycled into the HMS pathway for regeneration into NADPH.

Figure 4:
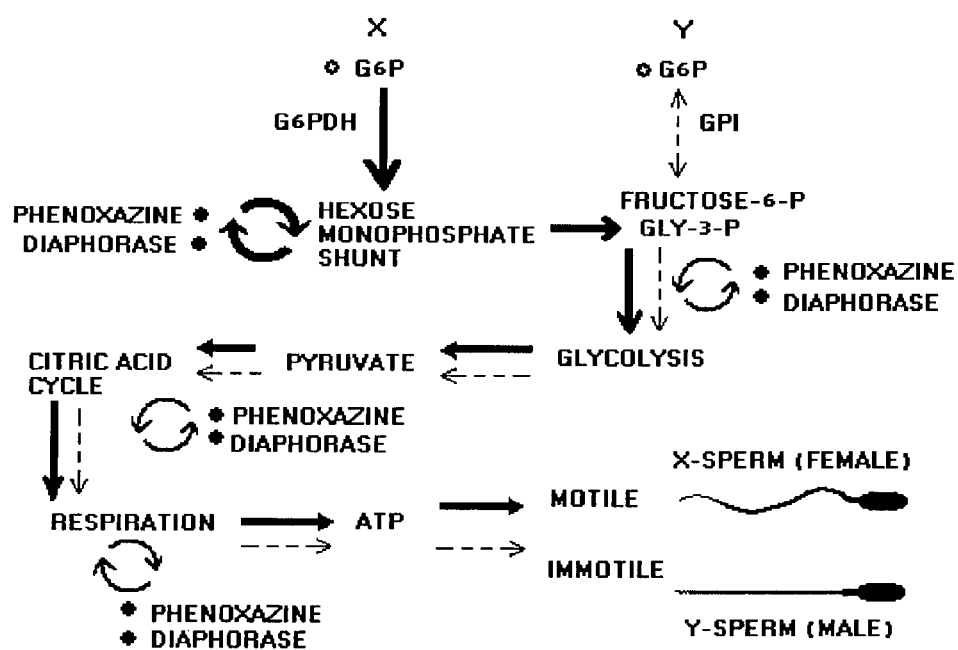
FIG. 4 is a schematic diagram of the metabolic pathways that are modified by the composition of matter embodied within this invention resulting in increased sperm function of the X-chromosome bearing sperm.

FIG. 4 illustrates how these three components initiate the biological response in the X and Y-chromosome bearing sperm. The transfers of electrons through the metabolic pathways of the X-chromosome bearing (female) sperm are represented by the solid dark arrows. When the semen mixture, containing relatively equivalent amounts of X and Y-bearing sperm, is exposed the substrate, G-6-P, the X-chromosome bearing sperm (represented by the X) are stimulated by the uptake of G-6-P to shunt the G-6-P into the HMS pathway. The phenoxazine-diaphorase "catalyst" begins the amplification of the HMS (represented by the dark circular arrows). The effect of the phenoxazine-diaphorase "catalyst" extends throughout the metabolic pathways to promote glycolysis, the citric acid cycle, oxidative phosphorylation, and respiration. The result is the generation of large amounts of NADPH, NADH, other metabolic precursors and ATP. This consequence is increased sperm function, motility, and fertility of the female sperm.

The transfers of electrons through the metabolic pathways of the Y-chromosome bearing (male) sperm are represented by the dotted-line arrows of FIG. 4. The Y-chromosome sperm (represented by the Y) does not have the X-linked enzyme, G6PDH. With little or no intercellular levels of the enzyme, the male sperm are unable to initiate metabolism of the G-6-P through the HMS pathway. The G-6-P is shunted directly into the glycolytic pathway. The diaphorase-phenoxazine catalyst would have somewhat limited effect due to absence of NADPH. The metabolic results would be a depletion of energy reserves and a gradual loss of sperm function, motility, and lower levels of fertilization capacity of the male sperm.

Upon insemination of the treated semen, the X-chromosome bearing (female) sperm with increased metabolic capacity relative the male sperm have a higher probability of successful fertilization. The result would be a shifting of the sex ratio in favor of female offspring.

Preparation of the Composition

The composition described above is fabricated employing numerous protocols. The biologically active nature of the components requires stabilization for maintenance of bioactivity. The composition of matter can be stabilized by lyophilization (drying), sulfate inhibition, or by freezing of a composition mixture. In one form, each compound of the composition is prepared and stored in separate instruments. Prior to use, each compound is mixed with a buffered solution in the appropriate concentrations to produce a reagent mixture. In another form of embodiment, the subject composition could be maintained in the liquid state and stabilized at temperatures at or below 0° C., usually below −15° C. or lower. In another embodiment, the individual aliquots of said composition could be mixed with the cell or sperm sample prior to freezing of the sperm sample. In other embodiments, the individual compounds of the composition are stabilized by lyophilization (freeze-drying) and packaged either in multiple, bulk or individual quantities of required aliquots. Prior to use, each compound is mixed in the appropriate concentrations to produce the composition. In other embodiments, the individual compounds of the composition are mixed to form a single composition prior to storage; stabilization is done by freezing as described in the above embodiment. Alternatively, the single composition could be stabilized by lyophilization (freeze-drying) in multiple, bulk, or individual quantities of required aliquots.

Composition in Kit Form

The invention includes a method of use of this invention in kit form. This embodiment requires the composition be prepared in unit dosage forms. For example, the composition is provided in concentrated form, either in solution or dried (lyophilized), packaged such that when a sperm sample is added to the composition container, and the resulting composition solution is of the appropriate physiological concentration. The mixture of sperm and composition are then incubated within the composition container (e.g., a 0.5 milliliter sample vial). Alternatively, the mixture can be returned to the semen container (e.g., a 0.5 milliliter semen straw) and incubated within the semen straw. Following contact of the sperm and said composition for the defined period of time and within the defined temperature, the sperm sample plus the composition are return to either the original or an unused insemination straw and inseminated directly into a receptive female.

A second embodiment of a kit requires that the composition be prepare in multiple dosages. That is, the composition is provided in concentrated form, either in solution or lyophilized, and packaged such that when a multiple sperm sample is added to the composition container, or the composition is added to the sperm sample, the resulting composition/semen solution is of the appropriate physiological concentration. Following contact of the sperm and said composition for the defined period of time and within the defined temperature, the sperm sample plus the composition are individually aliquot and packaged at the appropriate required sperm dosage. This embodiment could be used to prepare frozen gender-biased semen utilizing standard cryopreservation methodology. A second embodiment would be to prepare gender-biased semen without freezing for immediate use in an insemination program.

Methods of Use

In practicing the subject method, a sample of living sperm and the composition of matter are combined and incubated to form a reaction mixture during which the sperm are in contact with the composition. The reaction mixture is incubated under the appropriate conditions to maintain cell viability and/or sperm fertility. The temperature is generally at or near body temperature, e.g. 35-38° C. for cattle, and the time is generally less than 60 minutes but is experimentally determined, and varies with the species, sperm concentration, volume of the sperm sample, and with other factors such as type of diluent, and whether the sperm have been frozen, chilled, or freshly collected. The concentration of the composition is experimentally adjusted to the volume and titer of cell or sperm type. For example, commercially available bull semen is diluted with an extender, a buffered saline solution plus a cryoprotectant, gradually cooled, and frozen in liquid nitrogen and stored in single insemination doses of 2 to $50 \times 10^6$ living sperm in volumes of 0.25 milliliter or 0.50 milliliter. Dosage of the composition is adjusted to the volume of the semen sample and sperm concentration, such that the embodiment is maintained at a constant physiological concentration within the sperm storage medium.

Artisans familiar with the trade of artificial insemination, semen collection and processing, cell culture, and biochemistry would be able to mix, produce and reproduce these compositions following appropriate laboratory methodology, combination of compounds and of preparing cell medium.

EXAMPLE

The following example is included solely to provide a more complete disclosure of the invention described and claimed herein. The example does not limit the scope of the invention in any fashion.

Chemical and reagents were obtained commercially from Sigma-Aldrich Chemical (St. Louis, Mo., USA).

The preparation of the said composition includes brilliant cresol blue (FIG. 1) that requires the rehydration of physiological quantities: 100 mM BCB; NADP oxioreductase (0.1-1 unit/milliliter); and D-Glucose-6-phosphate (Nasalt) at physiological quantities (10-100 mM) rehydrated in modified Tyrodes albumin-lactate-pyruvate medium (TALP) buffered solution pH 7.4.

The components of the composition are mixed to form a rehydrated reaction mixture and added a sample of sperm usually in the form of a commercially available frozen-thawed semen sample. As an example, cattle semen is processed and stored (usually frozen) in single insemination doses at a volume of 0.25 milliliter, 0.50 milliliter or 1.0 milliliter and prepared in a commercially available semen extender, i.e. a buffered saline solution containing essential salts, energy substrates, a protein source, a cryoprotectant, and antibiotics. The components of commercially available semen extenders are well documented in the scientific literature.

The mixture of extended semen and the composition of this invention were incubated for 20 minutes at 35-37° C. Following incubation, the exposed semen was washed according to standard methods for in vitro fertilization. The standard 2-step Percoll gradient (90% and 55%) was modified for sperm washing by the addition of 100 mm G-6-P and 1 U/milliliter of diaphorase. Following centrifugation, the motile sperm fraction was used for in vitro insemination of bovine oocytes. Fertilized oocytes were cultured according to standard methods for bovine embryos for 5-7 days. These were sexed at day 5-7 using a standard PCR embryo sexing protocol. Control sperm underwent the same washing process without exposure to the composition of this invention. Data was pooled over 20 repetitions/N=500 and the average % of female embryo were as follows: Control, 48% female embryos; Treated, 70% female embryos.

Data from super-ovulated donors and from gender of calves resulting from the artificial insemination of semen treated with the said composition of matter have shown an increase in the percentage of females resulting from the treated semen. The normal sex ratio of cattle at birth is usually 52/48, i.e., 52% male and 48% female. With use of this invention, the sex ratio is repeatedly shifted in favor of females and increased by 20-38%.

What I claim as my invention is:

1. A method to produce female offspring in mammals, the method comprising
   (a) contacting a sperm sample with a composition of matter consisting of the phenoxazine, brilliant cresyl blue; the phosphorylated hexose sugar, D-glucose-6-phosphate; and the oxidoreductase enzyme, NADH/NADPH diaphorase,
   (b) wherein, the amount of said composition is 100 mM of the phenoxazine, brilliant cresol blue, and 100 mM of the phosphorylated hexose ester, D-glucose-6-phosphate, and 1 unit per milliliter of the oxidoreductase enzyme, NADH/NADPH diaphorase,
   (c) wherein the sperm sample and composition are in contact for about 15 minutes, at a temperature between 35 degrees and 39 degrees Celsius,
   (d) wherein the sperm and composition are inseminated into a receptive female.

2. The method of claim 1, wherein a receptive female is inseminated to produce an embryo.

3. The method of claim 1, wherein an in vitro fertilization system is inseminated to produce an embryo.

4. The method of claim 1, wherein the sperm are cryopreserved in the presence of the composition.

5. A kit for producing female offspring in mammals, the kit comprising a 0.5 milliliter container, wherein a composition of matter is lyophilized within the container, wherein the composition of matter consisting of 100 mM of brilliant cresyl blue, and 100 mM of glucose-6-phosphate, and 1 unit/milliliter of NADPH oxidoreductase, wherein a 0.5 milliliter sperm sample is introduced into the container, wherein the sperm sample is in contact with the composition at a temperature of 35 degrees Celsius, wherein after 15 minutes the sperm sample and composition are removed, wherein the sperm sample and composition are inseminated into a receptive female; and instruction for use of the kit.

* * * * *